United States Patent [19]

Garland et al.

[11] Patent Number: 5,672,743

[45] Date of Patent: Sep. 30, 1997

[54] PROCESS FOR THE PRODUCTION OF ACETIC ACID

[75] Inventors: Carl Sherman Garland, Columbia, Md.; Martin Francis Giles, Middlesex; John Glenn Sunley, North Humberside, both of England

[73] Assignee: BP Chemicals Limited, London, England

[21] Appl. No.: 284,078

[22] Filed: Aug. 1, 1994

[30] Foreign Application Priority Data

Sep. 10, 1993 [GB] United Kingdom ............... 9318809
May 5, 1994 [GB] United Kingdom ............... 9408966

[51] Int. Cl.$^6$ ............................ C07C 51/10; C07C 51/12
[52] U.S. Cl. .................................................. 562/519
[58] Field of Search ........................................ 562/519

[56] References Cited

U.S. PATENT DOCUMENTS

| | | | |
|---|---|---|---|
| 3,285,948 | 11/1966 | Butter | 260/642 |
| 3,772,380 | 11/1973 | Paulik et al. | |
| 3,813,428 | 5/1974 | Paulik et al. | 260/532 |
| 4,029,748 | 6/1977 | Forster et al. | 423/418 |
| 4,046,807 | 9/1977 | Kuckertz | 260/549 |
| 4,101,450 | 7/1978 | Hwang et al. | 252/460 |
| 4,102,921 | 7/1978 | Bartish | 260/532 |
| 4,136,104 | 1/1979 | Hwang et al. | 260/449 R |
| 4,333,884 | 6/1982 | Kübbeler et al. | 260/546 |
| 4,356,126 | 10/1982 | Drent | 260/410.9 R |
| 4,430,273 | 2/1984 | Erpenbach et al. | 260/546 |
| 4,484,002 | 11/1984 | Lin | 560/232 |
| 4,487,406 | 12/1984 | Steinmetz et al. | 560/80 |
| 4,500,474 | 2/1985 | Gauthier-Lafaye et al. | 260/549 |
| 4,514,336 | 4/1985 | Ryan et al. | 260/413 |
| 4,519,956 | 5/1985 | Lin et al. | 260/549 |
| 4,588,834 | 5/1986 | Larkin | 560/233 |
| 4,629,809 | 12/1986 | Vanderpool et al. | 562/519 |
| 4,640,802 | 2/1987 | Drent | 260/410.9 R |
| 4,658,053 | 4/1987 | Green | 560/234 |
| 4,661,623 | 4/1987 | Chang et al. | |
| 4,664,851 | 5/1987 | Drent | 260/410.9 R |
| 4,681,707 | 7/1987 | Alper | 260/410.9 R |
| 4,997,978 | 3/1991 | Gauthier-Lafaye et al. | 560/265 |
| 5,268,505 | 12/1993 | Delis et al. | 562/517 |

FOREIGN PATENT DOCUMENTS

| | | |
|---|---|---|
| 38037/89 | 1/1990 | Australia. |
| 1234150 | 3/1988 | Canada. |
| 1258469 | 8/1989 | Canada. |
| 1267129 | 3/1990 | Canada. |
| 0 031 606 | 7/1981 | European Pat. Off.. |
| 0 072 055 | 2/1983 | European Pat. Off.. |
| 0 075 335 | 3/1983 | European Pat. Off.. |
| 0 075 337 | 3/1983 | European Pat. Off.. |
| 0 083 121 | 7/1983 | European Pat. Off.. |
| 0 090 443 | 10/1983 | European Pat. Off.. |
| 0 120 631 | 10/1984 | European Pat. Off.. |
| 0 131 998 | 1/1985 | European Pat. Off.. |
| 0 155 122 | 9/1985 | European Pat. Off.. |
| 0618183 | 10/1994 | European Pat. Off.. |
| 19 41 449 | 3/1970 | Germany. |
| 19 41 448 | 4/1970 | Germany. |
| 1767150B2 | 5/1972 | Germany. |
| 56-083439-A | 7/1981 | Japan. |
| 58-167531-A | 10/1983 | Japan. |
| 58-172331-A | 10/1983 | Japan. |
| 60-032724-A | 2/1985 | Japan. |
| 60-032726-A | 2/1985 | Japan. |
| 60-199841 | 10/1985 | Japan. |
| 60-255741-A | 12/1985 | Japan. |
| 62-135445-A | 6/1987 | Japan. |
| 3197441-A | 8/1991 | Japan. |
| 4046139-A | 2/1992 | Japan. |
| 1234641 | 6/1971 | United Kingdom. |
| 1234642 | 6/1971 | United Kingdom. |
| 1276326 | 6/1972 | United Kingdom. |
| 1448010 | 9/1976 | United Kingdom. |
| 1450993 | 9/1976 | United Kingdom. |
| 1523346 | 8/1978 | United Kingdom. |
| 2029409 | 3/1980 | United Kingdom. |

OTHER PUBLICATIONS

J. Mol. Catal., 85 (1993) L109–L116.

"Carbonylation of the Ru–Me Bond of Ru(Me) (I) $(CO)_2(^iPr-N=CHCH=N-^iPr)$ Catalyzed by $Ru(CO)_4(PR_3)$, $ZnCl_2$, and $H^{+}$"; *Organometallics*; Marco J. A. Kraakman et al.; 11, 3774–3785 (© 1992).

"Ruthenium–Catalyzed Carbonylation Reactions of Alcohols to Acids and Esters" *Journal of Molecular Catalysis*; G. Jenner et al.; 40 (1987) 71–82.

"$C_1$ to Acetyls: Catalysis and Process"; *Catalysis Today*; M. J. Howard et al.; 18 (1993) 325–354.

"Methanol Carbonylation to Acetic Acid"; *Applied Industrial Catalysis*, vol. 1; R. Eby and T. Singleton; (1983) 275–296.

Abstract for Schrod & Luft; 27th DGMK Annu. Meet. (Aachen Oct. 6–8 1982) (Condens.) (Dtsch. Ges.). Chem. Lett. (9) 1611–12.

"Methanol and Carbonylation"; *Rhône–Poulenc Recherches*; J. Gauthier–Lafaye et al.; (1987) 136–201.

"Kinetic and Spectroscopic Studies of the Carbonylation of Methanol with an Iodide–Promoted Iridium Catalyst"; D. Forster; (1979) 1639–1645.

"Halide Catalysis of the Oxidative Addition of Alkyl Halides to Rhodium(I) Complexes"; *JACS*; D. Forster; (1975) 97:4, 951–952.

(List continued on next page.)

*Primary Examiner*—Jose'G. Dees
*Assistant Examiner*—Rosalynd A. Williams
*Attorney, Agent, or Firm*—Brooks Haidt Haffner & Delahunty

[57] ABSTRACT

A process for the production of acetic acid by carbonylation of methanol or a reactive derivative thereof by contacting the methanol or derivative with carbon monoxide in a liquid reaction composition comprising (a) acetic acid, (b) an iridium catalyst, (c) methyl iodide, (d) at least a finite quantity of water and (e) methyl acetate is improved by the use as promoter of at least one of ruthenium and osmium.

29 Claims, No Drawings

OTHER PUBLICATIONS

"Mechanistic Study of Methanol Carbonylation Catalyzed by an Iridium Complex in the Presence of Methyl Iodide"; *Journal of Catalysis*; T. Matsumoto et al.; 51 (1978) 96–100.

"Further Study of Methanol Carbonylation Catalyzed by Cobalt, Rhodium, and Iridium Catalysts"; *Bulletin of the Chemical Soceity of Japan*; T. Mizoroki et al.; 52 (1979) 479–482.

"Mechanistic Pathways in the Catalytic Carbonylation of Methanol by Rhodium and Iridium Complexes"; *Advances in Organometallic Chemistry*; D. Forster; 17 (1979) 255–267.

"Homogeneous Catalytic Reactions of Methanol with Carbon Monoxide"; *Journal of Molecular Catalysis*; D. Forster; 17 (1982) 299–314.

"Mechanistic Aspects of Transition–Metal–Catalyzed Alcohol Carbonylations"; *Adv. in Catal.*; T. Dekleva and D. Forster; 34 (1986) 81–130.

"Carbonylation of Ethanol Using Monogeneous Ir Complex Catalyst: Effect of Ligands and Reaction Conditions"; *Journal of Molecular Catalysis*; R. P. Patil et al.; 47 (1988) 87–97.

"Carbonylation of Ethanol Using Homogeneous Iridium Complex Catalyst: A Kinetic Study"; *Journal of Molecular Catalysis*; R. P. Patil et al.; 72 (1992) 153–165.

"Chemists Detail Catalysis Work with $C_1$ Systems"; *C & EN*; Joseph Haggin; (1984) 21–22.

PROCESS FOR THE PRODUCTION OF ACETIC ACID

The present invention relates to a process for the production of acetic acid by carbonylation of methanol or a reactive derivative thereof in the presence of an iridium catalyst and as promoter, at least one of ruthenium and osmium.

Carbonylation processes in the presence of iridium catalysts are known and are described for example in U.S. Pat. No. 3772380. UK patent GB 1276326 describes preparation of monocarboxylic acids and their esters by carbonylation of alcohols, halides, ethers, esters or 1,2 epoxy aliphatic compounds in the presence of rhodium or iridium catalysts, halogen promoters and water or an alcohol, ether or ester.

Carbonylation processes in the presence of ruthenium and osmium catalysts are also known. Thus, UK patents GB 1234641 and GB 1234642 describe a process for the production of an organic acid or an ester by carbonylation of an alcohol, halide, ester, ether or phenol in the presence of a noble metal catalyst selected from iridium, platinum, palladium, osmium and ruthenium and their compounds and a promoter which is halogen or halogen compound. According to Jenner et al in J.Mol. Catalysis 40 (1987) 71–82 ruthenium compounds are effective carbonylation catalyts for converting primary alcohols into acids and esters at high CO pressures. Standard conditions of 450 bar CO pressure were used in the reported experiments and low CO pressures were said to lead to high yields of hydrocarbons and a lower yield of ester. UK patent application GB 2029409 describes a process for the preparation of aliphatic carboxylic acids and esters by reacting carbon monoxide with alcohols at an elevated pressure of 34 atmospheres or greater in the presence of a ruthenium catalyst and halogen-containing promoter.

U.S. Pat. No. 5268505 describes the preparation of adipic acid by hydrocarboxylating a pentenic acid in the presence of rhodium catalyst and a co-catalyst of at least one of iridium, ruthenium and osmium.

European patent publication EP 0031606-A describes a process for the co-production of carboxylic acids and esters by reaction of esters and/or ethers with carbon monoxide and hydrogen in the presence of a catalyst system which comprises a ruthenium compound, a Group II metal iodide and/or bromide or transition metal iodide and/or bromide, and a further Group VIII metal compound. The Group VIII metal is said to be especially rhodium and palladium. Only these Group VIII metals are illustrated in the examples.

According to European patent publications EP 0075335-A and EP 0075337-A the Group II or transition metal iodide and/or bromide in the catalytic system of EP 0031606-A can be replaced by methyl iodide or bromide or acetyl iodide or bromide or any mixture thereof provided that the reaction is carried out in the presence of an amine or phosphine respectively in an amount not exceeding a certain level. The use of iridium is not disclosed.

It has now been found that ruthenium and/or osmium have beneficial effects on the rate of carbonylation of methanol or a reactive derivative thereof in the presence of an iridium catalyst.

Thus, according to the present invention there is provided a process for the production of acetic acid by carbonylation of methanol and/or a reactive derivative thereof which process comprises contacting methanol and/or a reactive derivative thereof with carbon monoxide in a liquid reaction composition in a carbonylation reactor characterised in that the liquid reaction composition comprises: (a) acetic acid, (b) an iridium catalyst, (c) methyl iodide, (d) at least a finite concentration of water, (e) methyl acetate and (f) as promoter, at least one of ruthenium and osmium.

Also according to the present invention there is provided a catalyst system for the production of acetic acid by carbonylation of methanol or a reactive derivative thereof in the presence of at least a finite concentration of water which catalyst system comprises: (a) an iridium catalyst, (b) methyl iodide and (c) at least one of ruthenium and osmium.

Suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition, of methyl acetate is suitably in the range 1 to 70% by weight, preferably 2 to 50% by weight, most preferably 3 to 35% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water in the liquid reaction composition is in the range 0.1 to 15% by weight, more preferably 1 to 15% by weight, most preferably 1 to 10% by weight.

The iridium catalyst in the liquid carbonylation reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2BR]_2$, $[Ir(CO)_2I_2]^-$, $[Ir(CO)_2BR_2]^-$, $[Ir(CO)_4I_2]^-$, $[Ir(CH_3)I_3(CO)_2]^-$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate $[Ir_3O(OAc)_6(H_2O)_3][OAc]$, and hexachloroiridic acid $[H_2IrCl_6]$ preferably, chloride-free complexes of iridium such as acetates, oxalates and acetoacetates.

Preferably, the iridium catalyst concentration in the liquid reaction composition is in the range 100 to 6000 ppm by weight of iridium.

The ruthenium and/or osmium promoter may comprise any ruthenium and/or osmium containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, tetra (aceto)chlororuthenium(II,III), ruthenium (III) acetate, ruthenium (III) propionate, ruthenium (III) butyrate, ruthenium pentacarbonyl, triruthentiumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium(II), tetrachlorobis (benzene)diruthenium(II), dichloro(cycloocta-1,5-diene) ruthenium (II) polymer and tris(acetylacetonate)ruthenium (III).

Examples of suitable osmium containing compounds which may be used include osmium (III) chloride hydrate and anhydrous, osmium metal, osmium tetraoxide, triosmiumdodecacarbonyl, pentachloro-μ- nitrododiosmium and mixed osmium halocarbonyls such as tricarbonyldichloroosmium (II) dimer and other organoosmium complexes.

The molar ratio of each promoter to iridium catalyst is suitably in the range 0.1:1 to 15:1, preferably 0.5:1 to 10:1.

Preferably, the concentration of methyl iodide in the liquid reaction composition is in the range 1 to 20% by weight, preferably 2 to 15% by weight.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the reaction is suitably in the range 1 to 70 bar preferably 1 to 35 bar and most preferably 1 to 15 bar.

The catalyst system of the present invention has been found to be particularly beneficial at relatively low partial pressures of carbon monoxide where the rate of reaction may be dependent upon the carbon monoxide partial pressure. Under these conditions, it has been found that the catalyst system of the present invention has the advantage of providing an increased rate of reaction over catalyst systems without the promoters of the present invention. This advantage allows for increased rate of reaction under conditions when the carbon monoxide partial pressure is relatively low, for example due to a low total pressure in the carbonylation reactor or due to high vapour pressure of components of the liquid reaction composition, for example at high methyl acetate concentration in the liquid reaction composition or due to a high concentration of inert gases (for example nitrogen and carbon dioxide) in the carbonylation reactor. The catalyst system may also have advantages of increasing rate of carbonylation when the rate of reaction is reduced by the availability of carbon monoxide in solution in the liquid reaction composition resulting from mass transfer limitations, for example due to poor agitation.

Under some conditions it is believed possible that small amounts of the iridium catalyst may be volatile. It is believed that the presence of at least ruthenium may reduce the volatility of the iridium catalyst. Also, the use of ruthenium or osmium promoter, by increasing the carbonylation rate may allow operation at reduced iridium concentration which can have benefits for reduced by-product formation.

The pressure of the carbonylation reaction is suitably in the range 10 to 200 barg, preferably 10 to 100 barg, most preferably 15 to 50 barg. The temperature of the carbonylation reaction is suitably in the range 100° to 300° C., preferably in the range 150° to 220° C.

Acetic acid may be used as a solvent for the reaction.

Corrosion metals, particularly nickel, iron and chromium should be kept to a minimum in the liquid reaction composition as these may have an adverse effect in the reaction.

The process of the present invention may be performed as a batch or continuous process, preferably as a continuous process.

The acetic acid product may be removed from the reactor by withdrawing liquid reaction composition and separating the acetic acid product by one or more flash and/or fractional distillation stages from the other components of the liquid reaction composition such as iridium catalyst, ruthenium and/or osmium promoter, methyl iodide, water and unconsumed reactants which may be recycled to the reactor to maintain their concentrations in the liquid reaction composition. The carboxylic acid and/or ester product may also be removed as a vapour from the reactor.

The invention will now be illustrated by way of example only by reference to the following examples.

In the examples reaction rates are quoted as number of moles of product/reactant produced/consumed per liter of cold degassed reactor composition per hour (mol/l/hr).

A 150 ml Hastelloy B2 (Trade Mark) autoclave equipped with a Magnedrive (Trade Mark) stirrer and liquid injection facility was used for a series of batch carbonylation experiments. A gas supply to the autoclave was provided from a gas ballast vessel, feed gas being provided to maintain the autoclave at a constant pressure and the rate of gas uptake being calculated (with an accuracy believed to be ±1%) from the rate at which the pressure falls in the gas ballast vessel.

At the end of each experiment liquid and gas samples from the autoclave were analysed by gas chromatography.

For each batch carbonylation experiment the autoclave was charged with the ruthenium or osmium promoter and the liquid components of the liquid reaction composition excluding part of the acetic acid and water charge, in which the iridium catalyst was dissolved.

The autoclave was flushed once with nitrogen and once with carbon monoxide and was then heated with stirring (1000 rpm) to 195° C. After allowing the system to stabilise for about 30 minutes, the iridium catalyst in acetic acid/water solution was then injected into the autoclave under pressure of carbon monoxide. The pressure in the autoclave was subsequently maintained at 30 barg with carbon monoxide fed from the gas ballast vessel through the liquid injection facility.

Gas uptake from the ballast vessel was measured every 30 seconds and from this was calculated the rate of carbonylation, expressed as moles of carbon monoxide per liter of liquid reaction composition per hour (mol/l/hr). After uptake of carbon monoxide from the ballast vessel had ceased the autoclave was isolated from the gas supply, was cooled to room temperature and the gases were vented from the autoclave, sampled and analysed. The liquid reaction composition was discharged from the autoclave and was analysed for liquid products and by-products.

To obtain a reliable baseline a number of identical baseline runs may have to be performed to condition the autoclave such that consistent rates are achieved. This conditioning period is often different from autoclave to autoclave and may depend upon its previous history. An induction period is also sometimes observed, particularly at low pressure in the absence of any promoters. This induction period is not present when the promoters of the present invention are present.

EXPERIMENT A

A baseline experiment was performed with the autoclave charged with methyl acetate (419 mmol), water (383 mmol), methyl iodide (27 mmol), and acetic acid (806 mmol).

The iridium catalyst solution comprised $IrCl_3.3H_2O$ (0.54 mmol) dissolved in acetic acid (83 mmol) and water (50 mmol).

The reaction was performed at a constant pressure of 30 barg and at a temperature of 195° C. The rate of reaction, measured 5 minutes after injection of the iridium catalyst solution, based upon carbon monoxide uptake rate was 9.8 mol/l/hr. High conversion to acetic acid was observed with only 20 mmol methyl acetate remaining in the liquid reaction composition at the end of the experiment. The non-condensible gases in the autoclave at room temperature at the end of the experiment were analysed and were found to contain by volume, 3.6% carbon dioxide and 1.6% methane, the balance comprising hydrogen (not measured) and carbon monoxide.

This is not an example according to the present invention because no ruthenium or osmium promoter was present in the liquid reaction composition.

EXPERIMENT B

Experiment A was repeated. The reaction rate, measured in an identical manner to Experiment A was 10.1 mol/l/hr. The amount of methyl acetate remaining in the liquid reaction composition at the end of the experiment was 25 mmol.

The vented gas at the end of the experiment was analysed as in Experiment A and was found to contain 1.5% carbon dioxide and 1.1% methane.

EXAMPLE 1

Experiment A was repeated with dichlorotricarbonyl ruthenium (II) dimer (0.54 mmol) charged to the autoclave at the start before the iridium catalyst solution was added. The total amount of acetic acid charged (884 mmol) was adjusted so that the percentage concentrations by weight of the iridium catalyst, methyl acetate, methyl iodide and water were the same as in Experiments A and B.

The rate of reaction based upon carbon monoxide uptake, measured 5 minutes after injection of the catalyst solution was 11.7 mol/l/hr which is about 19% and 16% higher than the rates measured in Experiments A and B respectively.

The liquid reaction composition at the end of the experiment was analysed and was found to contain 17.7 mmol methyl acetate. The gas vented at the end of the experiment was found to contain by volume 0.7% methane and 0.6% carbon dioxide.

This Example is according to the present invention and shows the benefit of the presence of ruthenium in the liquid reaction composition on the carbonylation rate.

EXAMPLE 2

Example 1 was repeated except that 1.6 mmol of 15 dichlorotricarbonyl ruthenium (II) dimer and 880 mmol of acetic acid were charged to the autoclave.

The rate of reaction based upon carbon monoxide uptake, measured 5 minutes after injection of the catalyst, was 15.7 mol/l/hr which is about 60% and 55.5% higher than the rates measured in Experiments A and B respectively.

The liquid reaction composition at the end of the experiment contained 13.8 mmol methyl acetate.

The gas vented at the end of the experiment contained by volume 1.3% methane and 1.9% carbon dioxide.

This Example is according to the present invention and shows the benefit of an increase in the concentration of ruthenium in the liquid reaction composition on the carbonylation rate.

EXAMPLE 3

Example 1 was repeated except that 2.7 mmol of dichlorotricarbonyl ruthenium (II) dimer and 876 mmol of acetic acid were charged to the autoclave.

The rate of reaction based upon carbon monoxide uptake, measured 5 minutes after injection of the catalyst solution, was 16.5 mol/l/hr which is about 68% and 63% higher than the rates measured in the baseline Experiments A and B respectively.

The liquid reaction composition at the end of the experiment contained 6.4 mmol methyl acetate.

The gas vented at the end of the experiment contained by volume 1.1% methane and 1.1% carbon dioxide.

This Example is according to the present invention and shows the benefit of a further increase in the concentration of ruthenium in the liquid reaction composition on the carbonylation rate.

EXAMPLE 4

Example 1 was repeated except that 3.8 mmol of dichlorotricarbonyl ruthenium (II) dimer and 871 mmol of acetic acid were charged to the autoclave.

The rate of reaction based upon carbon monoxide uptake, measured 5 minutes after injection of the catalyst solution was 15.9 mol/l/hr which is about 62% and 57.5% higher than the rates measured in the baseline Experiments A and B respectively.

The liquid reaction composition at the end of the experiment contained 8.7 mmol methyl acetate.

The gas vented at the end of the experiment contained by volume 1.5% methane and 2.2% carbon dioxide.

This Example is according to the present invention and shows that, at least under the reaction conditions given in Experiments A and B, the increase in reaction rate with increasing ruthenium concentration reached a maximum.

EXAMPLE 5

Example I was repeated except that 5.4 mmol of dichlorotricarbonyl ruthenium (II) dimer and 802 mmol of acetic acid were charged to the autoclave.

The rate of reaction based upon carbon monoxide uptake, measured 5 minutes after injection of the catalyst solution was 15.1 mol/l/hr which is about 54% and 49.5% higher than the rates measured in Experiments A and B respectively.

The liquid reaction composition at the end of the reaction contained 5.2 mmol methyl acetate.

The gas vented at the end of the experiment contained by volume 1.9 % methane and 2.8% carbon dioxide.

This Example is according to the present invention and shows that, at least under the reaction conditions given in Experiments A and B, that above a certain concentration of ruthenium the degree of rate enhancement began to decline.

EXPERIMENT C

The autoclave was charged with methyl acetate (420 mmol), water (434 mmol), methyl iodide (27 mmol), acetic acid (802 mmol) and dichlorotricarbonyl ruthenium (II) dimer (4.1 mmol). No iridium catalyst solution was added to the autoclave.

The autoclave was heated at 195° C. at a constant pressure of 30 barg for about 1 hour but no uptake of carbon monoxide gas from the ballast vessel was observed.

The amount of methyl acetate in the liquid reaction composition at the end of the experiment was measured to be about 338 mmol (this might be subject to some degree of calibration error at this high level).

The non-condensable gases in the autoclave at room temperature at the end of the experiment were analysed as before and contained, by volume, 0.4% methane and 0.4% carbon dioxide.

This is not an example according to the present invention because no iridium catalyst was present in the liquid reaction composition. This example shows that ruthenium alone did not act as a catalyst for the carbonylation of methyl acetate.

EXPERIMENT D

Experiments A and B were repeated at higher methyl iodide concentration. The autoclave was charged with methyl acetate (420 mmol), water (384 mmol), methyl iodide (56 mmol), and acetic acid (737 mmol). The amount of acetic acid was adjusted so that the percentage concentrations by weights of iridium catalyst, methyl acetate and water were the same as in Experiments A and B.

The rate of reaction based upon carbon monoxide uptake, measured 5 minutes after injection of the catalyst solution was 12.2 mol/l/hr.

The liquid reaction composition at the end of the experiment was analysed and contained 8.5 mmol methyl acetate.

The gas vented at the end of the experiment contained by volume 1.4% methane and 2.4% carbon dioxide.

This experiment is not an example according to the present invention because no promoter was present in the liquid reaction composition.

EXAMPLE 6

Experiment D was repeated with dichlorotricarbonyl ruthenium (II) dimer (5.4 mmol) charged to the reactor at the start before the catalyst was added. The total amount of acetic acid charged (796 mmol) was adjusted so that the percentage concentrations by weight of the iridium catalyst, methyl acetate, methyl iodide and water were the same as in Experiment D.

The rate of reaction based upon carbon monoxide uptake, measured 5 minutes after injection of the catalyst solution was 23.9 mol/l/hr which is about 96% higher than the rate measured in comparative Experiment D.

The liquid reaction composition at the end of the experiment was analysed and was found to contain 7.3 mmol methyl acetate.

The gas vented at the end of the experiment contained by volume 1.4% methane and 2.4% carbon dioxide.

This experiment is an example according to the present invention and shows that at a higher methyl iodide concentration ruthenium was more effective as a promoter for the iridium catalysed carbonylation of methyl acetate.

EXPERIMENT E

The autoclave was charged with methyl acetate (420 mmol), water (430 mmol), methyl iodide (57 mmol), acetic acid (871 mmol) and dichlorotricarbonyl ruthenium (II) dimer (5.4 mmol). No iridium catalyst solution was added to the autoclave.

The autoclave was heated at 195° C. at a constant pressure of 30 barg for about 1 hour but no uptake of carbon monoxide gas from the ballast vessel was observed.

The amount of methyl acetate in the liquid reaction composition at the end of the experiment was measured as previously to be about 357 mmol.

The non-condensable gases in the autoclave at room temperature at the end of the experiment were analysed and were found not to contain any methane or carbon dioxide.

This is not an example according to the present invention because no iridium catalyst was present in the liquid reaction composition. This example shows that ruthenium alone did not act as a catalyst for the carbonylation of methyl acetate under the conditions of this experiment.

EXAMPLE 7

The autoclave was charged with methyl acetate (419 mmol), water (434 mmol), methyl iodide (27 mmol), acetic acid (864 mmol) and osmium trichloride $OsCl_3$ (0.54 mmol).

The autoclave was heated as previously at 195° C. at a constant pressure of 30 barg.

The reaction rate measured as previously was 13.9 mol/l/hr. The amount of methyl acetate in the liquid composition at the end of the experiment was measured to be 12.8 mmol. The methane and carbon dioxide were measured as previously to be 0.9% and 0.8% by volume respectively.

This is an example according to the present invention.

FURTHER EXPERIMENTS USING A SOLID INJECTION FACILITY

These further experiments were performed using a 150 ml Hastelloy B2 (Trade Mark) autoclave equipped with a Dispersimax (Trade Mark) stirrer, solid catalyst injection facility and cooling coils. A gas supply to the autoclave was provided from a gas ballast vessel, feed gas being provided to maintain the autoclave at a constant pressure. The rate of gas uptake at a certain point in a reaction run was used to calculate the rate at a particular reactor composition (reactor composition based on a cold degassed volume).

For each batch carbonylation experiment a small glass vial charged with the catalyst and optionally a catalyst promoter was placed in the injection facility which facility was fitted to the underside of the lid of the autoclave. The autoclave was sealed, pressure tested with nitrogen and flushed with carbon monoxide (2×3 barg). The liquid components of the reaction composition were then charged to the autoclave via a liquid addition port. The autoclave was then pressurised with carbon monoxide (typically 6 barg) and heated with stirring (1500 r.p.m.) to reaction temperature. The total pressure was then raised to approximately 4 barg below the desired operating pressure by feeding carbon monoxide from a ballast vessel. Once stable at temperature (15 minutes) the catalyst and optionally the catalyst promoter were injected using an overpressure of carbon monoxide. The reactor pressure was maintained constant (±0.5 barg) by feeding gas from the ballast vessel throughout the course of the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) controller. In addition, excess heat of reaction was removed by means of cooling coils.

At the end of each experiment liquid and gas samples from the autoclave were analysed by gas chromatography and water concentrations in liquid samples were determined by the Karl Fischer method.

Experiments F to H show how an iridium catalysed carbonylation reaction is affected by reduced total pressure of carbon monoxide and by reduced stirrer speed.

EXPERIMENT F

The batch autoclave was charged with methyl iodide (7.5 g, 0.053 moles), acetic acid (80 g, 1.33 moles), methyl acetate (48.1 g, 0.65 moles) and water (14 g, 0.780 moles). The autoclave was flushed with carbon monoxide and then pressurised with carbon monoxide to an ambient pressure of 6 barg. The autoclave contents were stirred (1500 r.p.m.) and heated to 195° C. Once stable at temperature the catalyst ($IrCl_3$.hydrate; 0.289 g, 0.78 mmoles) was introduced using an over pressure of carbon monoxide to give a reaction pressure of 20 barg. The reaction was carried out at constant pressure (20 barg) for a period of one hour. The experiment was repeated and the mean of the reaction compositions at the end of the two experiments is as follows:

85.1% Acetic Acid
3.9% Methyl Iodide
4.4% Methyl Acetate
5.7% Water

Trace levels of liquid by-products (ethyl iodide, ethyl acetate and propionic acid) and gaseous by-products carbon dioxide, hydrogen and methane were formed.

The methyl acetate concentrations in the liquid reaction compositions decreased during the two reactions and were calculated from the carbon monoxide uptakes as the reactions progressed. No allowance was made in these calculations for the partitioning of liquid reaction components to the vapour space of the autoclave, the compositions being calculated as cold degassed liquid.

When the methyl acetate concentrations were calculated to be 26% by weight the mean of the two experiments reaction rate was calculated to be 3.4 mol/l/hr. At 16% by weight methyl acetate concentration the mean reaction rate was 2.9 mol/l/hr.

This is not an example according to the present invention because no promoter was used.

EXPERIMENT G

Experiment F was repeated except that the total pressure in the autoclave was maintained at 28 barg after injecting the catalyst. The reaction was carried out at constant pressure (28 barg) for a period of one hour, yielding a solution containing the following distribution of products by weight:

88.5% Acetic Acid
3.2% Methyl Iodide
0.8% Methyl Acetate
5.3% Water

Trace levels of liquid by-products (ethyl iodide, ethyl acetate and propionic acid) and gaseous by-products (carbon dioxide, hydrogen and methane) were formed. When the methyl acetate concentration was calculated from gas uptake to be 26% by weight the reaction rate was calculated to be 10.0 mol/l/hr. At 16% by weight methyl acetate the reaction rate was 6.0 mol/l/hr.

This is not an example according to the present invention because no promoter was used.

EXPERIMENT H

This experiment illustrates the effect of stirrer speed on the carbonylation rate at a total pressure of 28 barg.

Experiment G was repeated except that the stirrer speed was reduced to 750 r.p.m.. When the methyl acetate concentration was calculated from gas uptake to be 26% by weight the reaction rate was calculated to be 6.5 mol/l/hr. At 16% by weight methyl acetate the reaction rate was 3.8 mol/l/hr.

EXAMPLE 8

This example demonstrates the promotional effect of introducing ruthenium promoter, one molar equivalent, to an iridium catalysed carbonylation at low total pressure.

Experiment F was repeated except that some of the acetic acid charge (0.20 g) was substituted with an equal weight of [{$Ru(CO)_3Cl_2$}$_2$] (0.39 mmoles), such that the total autoclave charge weight remained constant. The ruthenium was injected, together with the $IrCl_3$.hydrate. The reaction was carried out at constant pressure (20 barg) for a period of one hour, yielding a solution containing the following distribution of products by weight:

89.1% Acetic Acid
2.8% Methyl Iodide
3.5% Methyl Acetate
4.8% Water

Trace levels of liquid by-products (ethyl iodide, ethyl acetate and propionic acid) and gaseous by-products (carbon dioxide, hydrogen and methane) were formed.

When the methyl acetate concentration was calculated from gas uptake to be 26% by weight the reaction rate was calculated to be 8.1 mol/l/hr. At 16% by weight methyl acetate the reaction rate was 5.3 mol/l/hr. The rates quoted are the mean of two identical experiments.

EXAMPLE 9

This example demonstrates the promotional effect of introducing ruthenium promoter, two molar equivalents, to an iridium catalysed carbonylation at low total pressure.

Experiment F was repeated except that some of the acetic acid charge (0.40 g) was substituted with an equal weight of [{$Ru(CO)_3Cl_2$}$_2$] (0.78 mmoles), such that the total autoclave charge weight remained constant. The ruthenium was injected, together with the $IrCl_3$.hydrate. The reaction was carried out at constant pressure (20 barg) for a period of one hour.

When the methyl acetate concentration was calculated to be 26% by weight the reaction rate was calculated to be 8.7 mol/l/hr. At 16% by weight methyl acetate the reaction rate was 7.2 mol/l/hr.

EXAMPLE 10

This example demonstrates the promotional effect of introducing ruthenium promoter, half a molar equivalent, to an iridium catalysed carbonylation at low total pressure.

Experiment F was repeated except that some of the acetic acid charge (0.10 g) was substituted with an equal weight of [{$Ru(CO)_3Cl_2$}$_2$] (0.20 mmoles), such that the total autoclave charge weight remained constant. The ruthenium was injected, together with the $IrCL_3$.hydrate. The reaction was carried out at constant pressure (20 barg) for a period of one hour.

When the methyl acetate concentration was calculated to be 26% by weight the reaction rate was calculated to be 5.6 mol/l/hr. At 16% by weight methyl acetate the reaction rate was 4.5 mol/l/hr.

EXAMPLE 11

This example demonstrates the promotional effect of introducing ruthenium promoter, one molar equivalent, to an iridium catalysed carbonylation at reduced stirrer speed (750 r.p.m.).

Experiment H was repeated except that some of the acetic acid charge (0.20 g) was substituted with an equal weight of [{Ru(CO)$_3$Cl$_2$}$_2$] (0.39 mmoles), such that the total autoclave charge weight remained constant. The ruthenium was injected, together with the IrCL$_3$.hydrate. The reaction was carried out at constant pressure (28 barg), with the stirrer set at 750 r.p.m., for a period of one hour, yielding a solution containing the following distribution of products by weight:

91.5% Acetic Acid
2.8% Methyl Iodide
1.9% Methyl Acetate
4.1% Water

Trace levels of liquid by-products (ethyl iodide, ethyl acetate and propionic acid) and gaseous by-products (carbon dioxide, hydrogen and methane) were formed. When the methyl acetate concentration was calculated to be 26% by weight the reaction rate was calculated to be 10.5 mol/l/hr. At 16% by weight methyl acetate the reaction rate was 7.3 mol/l/hr.

The reactor charges are given in Table 1.

The gaseous and liquid product yields for Comparative Experiments F–H and Examples 8–11 are given in Tables 2a and 2b. These product yields are not directly comparative to those recorded for Comparative Examples A–G and Examples 1–7 because the autoclaves were different in particular being operated with different amounts of reagents and having different headspaces and stirrer speeds.

TABLE 1

REACTOR AUTOCLAVE CHARGES

| EXPERIMENT | COMPONENTS(g) | | | | |
|---|---|---|---|---|---|
| | Methyl Acetate | Acetic Acid | Water | Methyl Iodide | Promoter |
| F | 48.1 | 80.1 | 14.1 | 7.5 | — |
|   | 48.1 | 80.1 | 14.0 | 7.6 | — |
| G | 48.1 | 80.1 | 14.0 | 7.5 | — |
| H | 48.1 | 80.2 | 14.1 | 7.6 | — |
| 8 | 48.2 | 80.1 | 14.0 | 7.5 | 0.20 |
|   | 48.1 | 80.2 | 14.0 | 7.6 | 0.20 |
| 9 | 48.1 | 79.9 | 14.1 | 7.4 | 0.40 |
| 10 | 48.1 | 80.3 | 14.5 | 7.5 | 0.10 |
| 11 | 48.2 | 80.3 | 14.0 | 7.4 | 0.20 |
| 12 | 48.2 | 80.2 | 14.1 | 7.6 | 0.20 |
| 13 | 48.1 | 79.9 | 14.3 | 7.6 | 0.46 |

TABLE 2a

Gaseous Products in Off-gas

| Experiment | Gaseous By-products (% v/v) | | | Gaseous By-products (mmol) | | |
|---|---|---|---|---|---|---|
| | H$_2$ | CO$_2$ | CH$_4$ | H$_2$ | CO$_2$ | CH$_4$ |
| F* | 1.6 | 2.0 | 6.8 | 2.8 | 3.4 | 12.0 |
| G | 1.4 | 1.0 | 2.1 | 5.6 | 4.0 | 7.9 |
| H | 1.3 | 1.1 | 2.2 | 5.4 | 4.6 | 8.7 |
| 8* | 1.5 | 2.3 | 7.7 | 3.1 | 4.7 | 16.6 |
| 9 | 1.4 | 2.1 | 6.6 | 2.8 | 4.2 | 13.3 |
| 10 | 1.7 | 2.1 | 6.8 | 3.5 | 4.3 | 14.0 |
| 11 | 1.9 | 0.7 | 0.8 | 6.9 | 2.6 | 3.0 |

*Mean of two experiments.

TABLE 2b

Liquid Products by Weight

| Experiment | Ethyl iodide % | Ethyl acetate % | Propoionic Acid | Acetic Acid |
|---|---|---|---|---|
| F* | 0.02 | 0.01 | 0.02 | 85.1 |
| G | 0.05 | 0.03 | 0.03 | 88.5 |
| H | 0.03 | 0.02 | 0.03 | 92.2 |
| 8* | 0.07 | 0.02 | 0.03 | 89.1 |
| 9 | 0.04 | 0.01 | 0.04 | 90.2 |
| 10 | 0.02 | 0.02 | 0.02 | 88.8 |
| 11 | 0.09 | 0.02 | 0.06 | 91.5 |

*Mean of two experiments

EXAMPLE 12

This experiment illustrates the effect of adding ruthenium promoter, one molar equivalent, on the carbonylation rate at a total pressure of 28 barg. The experiment also illustrates that the relative promotional effect of addition of one molar equivalent of ruthenium is greater at lower total pressure such as 20 barg then at higher pressures such as 28 barg.

Experiment G was repeated except that some of the acetic acid charge (0.20 g) was substituted with an equal weight of [{Ru(CO)$_3$Cl$_2$}$_2$] (0.39 mmoles), such that the total autoclave charge weight remained constant. The ruthenium was injected, together with the IrCl$_3$.hydrate. The reaction was carried out at constant pressure (28 barg) for a period of one hour, yielding a solution containing the following distribution of products by weight:

88.8% Acetic Acid
3.0% Methyl Iodide
1.9% Methyl Acetate
5.3% Water

Trace levels of liquid by-products (ethyl iodide, ethyl acetate and propionic acid) and gaseous by-products (carbon dioxide, hydrogen and methane) were formed. When the methyl acetate concentration was calculated to be 26% by weight the reaction rate was calculated to be 11.3 mol/l/hr. At 16% w/w methyl acetate the reaction rate was 7.9 mol/l/hr. Table 3 below shows the levels of by-products.

TABLE 3

Experiment 12

| Gaseous By-products % by volume (mmol) | | | Liquid By-products % by weight | | |
|---|---|---|---|---|---|
| H$_2$ | CO$_2$ | CH$_4$ | EtI | EtOAc | Propionic Acid |
| 1.3 (4.5) | 1.0 (3.7) | 1.4 (4.9) | 0.11 | 0.01 | 0.04 |

Thus, a comparison of Example 8 against Experiment F shows that at 20 barg the rate of reaction at 26% by weight methyl acetate is 2.4 times greater with ruthenium promoter whereas at 28 barg a comparison of Example 12 against Experiment G shows the improvement with ruthenium in reaction rate at 26% by weight methyl acetate is only 1.1 times.

EXAMPLE 13

This example demonstrates the promotional effect of introducing osmium promoter, approximately two molar equivalents, to an iridium catalysed carbonylation at low total pressure.

Experiment F was repeated except that some of the acetic acid charge (0.46 g) was substituted with an equal weight of osmium trichloride hydrate (0.46 g), such that the total autoclave charge weight remained constant. The osmium was injected, together with the $IrCl_3$.hydrate. The reaction was carried out at constant pressure (20 barg) for a period of one hour, yielding a solution containing the following distribution of products by weight:

89.4% Acetic Acid
3.4% Methyl Iodide
2.2% Methyl Acetate
5.4% Water

Trace levels of liquid by-products (ethyl iodide, ethyl acetate and propionic acid) and gaseous by-products carbon dioxide, hydrogen and methane were formed.

When the methyl acetate concentration was calculated to be 26% by weight the reaction rate was calculated to be 8.4 mol/l/hr. At 16% w/w methyl acetate, the reaction rate was 6.6 mol/l/hr.

The by-product concentrations are shown in Tables 4 and 5 below.

TABLE 4

| Example 13 | | | | | |
|---|---|---|---|---|---|
| Gaseous By-products (% v/v) | | | Gaseous By-products (mmol) | | |
| $H_2$ | $CO_2$ | $CH_4$ | $H_2$ | $CO_2$ | $CH_4$ |
| 1.6 | 1.1 | 2.4 | 3.7 | 4.9 | 12.1 |

TABLE 5

| Example 13 Liquid by-products (% w/w) | | |
|---|---|---|
| Ethyl iodide | Ethyl acetate | Propionic Acid |
| 0.05 | 0.03 | 0.03 |

FURTHER EXPERIMENTS USING A LIQUID INJECTION FACILITY

These further experiments were performed using a 150 ml Hastelloy B2 (Trade Mark) autoclave equipped with a Dispersimax (Trade Mark) stirrer, a liquid catalyst injection facility and cooling coils. A gas supply to the autoclave was provided from a gas ballast vessel, feed gas being provided to maintain the autoclave at a constant pressure. The rate of gas uptake at a certain point in a reaction run was used to calculate the rate at a particular reactor composition (reactor composition based on a cold degassed volume).

For each batch carbonylation experiment the catalyst, dissolved in a portion of the acetic acid/water liquid reactor charge, was charged to the liquid injection facility. The autoclave was sealed, pressure tested with nitrogen and was vented via a gas sampling system. The autoclave was then flushed with carbon monoxide (2×3 barg). The liquid components of the reaction composition and optional catalyst promoter excluding the portion of the liquid reaction composition in which the catalyst was dissolved, were then charged to the autoclave via a liquid addition port. The autoclave was then pressurised with carbon monoxide (typically 6 barg) and heated with stirring (1500 rpm) to reaction temperature. The total pressure was then raised to approximately 3 barg below the desired operating pressure by feeding carbon monoxide from a ballast vessel. Once stable at temperature (about 15 minutes) the catalyst solution was injected using an overpressure of carbon monoxide. The reactor pressure was maintained constant (±0.5 barg) by feeding gas from the ballast vessel throughout the course of the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) controller. In addition, excess heat of reaction was removed by means of cooling coils.

At the end of each experiment liquid and gas samples from the autoclave were analysed by gas chromatography.

EXPERIMENT I

The batch autoclave was charged with methyl iodide (7.5 g, 0.053 moles), acetic acid (69 g, 1.15 moles), methyl acetate (48.0 g, 0.65 moles) and water (8.4 g, 0.47 moles). The autoclave was flushed with carbon monoxide and then pressurised with carbon monoxide to an ambient pressure of 12 barg. The autoclave contents were stirred (1500 rpm) and heated to 190° C. Once stable at temperature the total pressure was increased to 24 barg by feeding carbon monoxide from the ballast vessel. The catalyst ($H_2IrCl_6$; 0.97 g, 2.34 mmoles) dissolved in 8.6 g water and 7.5 g of acetic acid was then introduced using an over pressure of carbon monoxide to give a reaction pressure of 27.4 barg. The reaction was carried out at constant pressure (27.4 barg) for a period of one hour. The methyl acetate concentration in the liquid reaction composition was calculated from the carbon monoxide uptake as the reaction progressed. When the methyl acetate concentration was calculated to be 26% by weight the reaction rate was calculated to be 16.5 mol/l/hr. At 16% by weight methyl acetate concentration the reaction rate was 11.8 mol/l/hr.

This is not an example according to the present invention because no promoter was used.

EXAMPLE 14

Experiment I was repeated except that the autoclave was charged with [{Ru(CO)$_3$Cl$_2$}$_2$] (0.60 g, 1.17 mmoles), methyl iodide (7.5 g, 0.053 moles), acetic acid (70.9 g, 1.18 moles), methyl acetate (48.0 g, 0.65 moles) and water (8.4 g, 0.466 moles). The catalyst ($H_2IrCl_6$; 0.97 g, 2.34 mmoles) was dissolved in 8.6 g water and 7.0 g acetic acid.

When the methyl acetate concentration was calculated to be 26% by weight the reaction rate was calculated to be 20.9 mol/l/hr. At 16% by weight methyl acetate concentration the reaction rate was 15.1 mol/l/hr.

EXPERIMENT J

The batch autoclave was charged with methyl iodide (8.6 g, 0.060 moles), acetic acid (67.9 g, 1.13 moles), methyl acetate (48.0 g, 0.65 moles) and water (8.4 g, 0.47 moles). The autoclave was flushed with carbon monoxide and then pressurised with carbon monoxide to an ambient pressure of 8 barg. The autoclave contents were stirred (1500 rpm) and heated to 190° C. Once stable at temperature the total pressure was increased to 17 barg by feeding carbon monoxide from the ballast vessel. The catalyst ($H_2IrCl_6$; 1.51 g, 3.72 mmoles) dissolved in 8.6 g water and 7.5 g acetic acid was then introduced using an overpressure of carbon monoxide to give a reaction pressure of 19.6 barg. The reaction was carried out at a constant pressure (19.6 barg) for a period of 36 minutes. The methyl acetate concentration in the liquid reaction composition was calculated from the carbon monoxide uptake as the reaction progressed. When the methyl acetate concentration was calculated to be 26% by weight the reaction rate was calculated to be 15.2 mol/l/hr. At 16 and 6% by weight methyl acetate concentration the reaction rate was 11.0 and 5.6 mol/l/hr respectively.

EXAMPLE 15

Experiment J was repeated except that the autoclave was charged with [{Ru(CO)$_3$Cl$_2$}$_2$] (0.95 g, 1.19 mmoles), methyl iodide (8.5 g, 0.06 moles), acetic acid (66.6 g, 1.10 moles), methyl acetate (48.0 g, 0.65 moles) and water (8.4 g, 0.46 moles). The autoclave was flushed with carbon monoxide and then pressurised with carbon monoxide to an ambient pressure of 6 barg. The autoclave contents were stirred (1500 rpm) and heated to 190° C. After about 15 minutes the pressure was increased to 17 barg by feeding carbon monoxide. The catalyst (H$_2$IrCl$_6$; 1.51 g, 3.72 mmoles) dissolved in 8.6 g water and 7.5 g acetic acid was then introduced using an overpressure of carbon monoxide to give a reaction pressure of 19.8 barg. The reaction was carried out at a constant pressure (19.8 barg) for a period of one hour.

When the methyl acetate concentration was calculated to be 26% by weight the reaction rate was calculated to be 26.5 mol/l/hr. At 16 and 6% by weight methyl acetate concentration the reaction rate was 20.9 and 12.8 mol/l/hr respectively. This experiment shows the promotional affect of the promoter even at low (6%) methyl acetate concentration.

EXPERIMENT K

Experiment J was repeated using methyl iodide (8.6 g 0.060 moles); acetic acid (67.6 g 1.13 moles), methyl acetate (48.0 g 0.65 moles) and water (8.4 g, 0.47 moles). After flushing and pressurising to 10 barg with carbon monoxide the reactor contents were stirred (1500 rpm) and heated to 190° C. before pressurising to 24 barg with carbon monoxide. The catalyst H$_2$IrCl$_6$ (1.51 g. 3.72 moles) dissolved in 8.6 g water and 7.5 g of acetic acid was introduced to give a pressure of 27.2 barg. The reaction was continued for 30 minutes. When the methyl acetate concentration was calculated to be 26% by weight the reaction rate was calculated to be 24.3 mol/l/hr; at 16% w/w methyl acetate the reaction rate was 17.0 mol/l/hr. This is not an example according to the present invention.

HIGH PRESSURE INFRARED EXPERIMENTS

A high pressure infrared cell equipped with a liquid injection facility was used in the following series of high pressure infrared experiments. A gas supply to the infrared cell was provided from a gas ballast vessel, feed gas being provided to maintain the high pressure infrared cell at a constant pressure and the rate of gas uptake being calculated from the rate at which the pressure falls in the gas ballast vessel.

Throughout the course of each experiment the liquid reaction composition was analysed by infrared spectroscopy.

At the end of each experiment liquid samples from the high pressure infrared cell were analysed by gas chromatography.

For each high pressure infrared experiment the high pressure infrared cell was charged with ruthenium promoter and the liquid components of the liquid reaction composition excluding a portion of the liquid components, in which the iridium catalyst was dissolved.

The high pressure infrared cell was flushed 3 times with carbon monoxide, pressurised with carbon monoxide to a pressure of 15 barg and heated to 190° C. with stirring. The system was allowed to stabilise for 15 minutes. The iridium catalyst solution was charged to the liquid injection facility and was then injected into the high pressure infrared cell under CO pressure. The pressure in the high pressure infrared cell was subsequently maintained at 27.5 barg with carbon monoxide fed from the gas ballast vessel through a back pressure regulator.

After uptake of carbon monoxide from the gas ballast vessel had ceased the contents of the high pressure infrared cell were cooled to room temperature and the gases vented from the high pressure infrared cell were sampled and analysed. The reaction composition was discharged from the high pressure infrared cell and was analysed for liquid products and by-products.

EXPERIMENT L

The liquid components of the initial liquid reaction composition consisted of methyl acetate (5.0 g), methyl iodide (1.0 g), water (2.05 g) and acetic acid (16.95 g).

The iridium catalyst solution consisted of IrCl$_3$.4H$_2$O (0.188 g) dissolved in a 2 ml portion of the liquid components of the liquid reaction composition.

The final liquid reaction composition was:

0.23 g Methyl Acetate
0.92 g Methyl Iodide
1.09 g Water
20.99 g Acetic Acid

Trace levels of liquid by-products (ethyl iodide, ethyl acetate and propionic acid) and gaseous by-products (carbon dioxide) were detected.

When the methyl acetate concentration was calculated from the carbon monoxide gas uptake to be 20% by weight the reaction rate was calculated to be 11.55 mol/l/hr. At 15 and 10% by weight methyl acetate concentrations the reaction rates were calculated to be 10.41 and 8.38 mol/l/hr respectively.

This is not an example according to the present invention because no promoter was used.

EXAMPLE 16

This example demonstrates the promotional effect of introducing ruthenium promoter, 2 molar equivalents, to an iridium catalysed carbonylation reaction. Experiment L was repeated except that [Ru(CO)$_3$Cl$_2$]$_2$ (0.266 g, Ir:Ru molar ratio of 2:1) was charged to a high pressure infrared cell. The final reaction composition was:

0.33 g Methyl Acetate
0.98 g Methyl Iodide
0.99 g Water
20.82 g Acetic Acid

The reaction rates at 20, 15 and 10% by weight methyl acetate concentrations were calculated to be 13.93, 12.88 and 10.42 mol/l/hr respectively (20.6, 23.0 and 24.3% increase in rate respectively compared with the corresponding rates in the absence of ruthenium promoter).

EXPERIMENT M

Experiment L was repeated except that the initial liquid components of the liquid reaction composition consisted of methyl acetate (15.0 g), methyl iodide (1.5 g), water (4.42 g) and acetic acid (9.01 g) to give a higher methyl acetate concentration. The iridium catalyst solution consisted of $IrCl_3.4H_2O$ (0.057 g) dissolved in a 2 ml portion of the liquid components of the liquid reaction composition.

The reaction rates at 30, 25, 20, 15 and 10% be weight methyl acetate concentrations were calculated to be 3.11, 2.74, 2.22, 1.75 and 1.28 mol/l/hr respectively.

EXAMPLE 17

Experiment M was repeated except that [{Ru(CO)$_3$Cl$_2$}$_2$] (0.42 g; Ir:Ru molar ratio of 5.5:1) was charged to the high pressure infrared cell.

The reaction rates at 30, 25, 20% by weight methyl acetate concentrations were all calculated to be 10.5 mol/l/hr.

The reaction rates at 15 and 10% by weight methyl acetate concentration were calculated to be 9.5 and 6.43 mol/l/hr respectively.

This example shows a promotional effect of the promoter at a high methyl acetate concentration.

FURTHER EXPERIMENTS (CONTINUOUS OPERATION)

Carbon monoxide was fed to a 300 ml Hastelloy (Trade Mark) autoclave equipped with a Dispersimax (Trade Mark) stirrer under pressure control (i.e. on demand) from a carbon monoxide supply line. A liquid feed comprising methanol, methyl iodide, catalyst, water, methyl acetate, acetic acid and optionally ruthenium promoter was pumped to the autoclave at a constant rate of typically 250 ml/hr from a feed tank. The composition of the liquid feed was chosen so as to give a desired reaction composition under steady state conditions (i.e. at a particular carbonylation rate and feed rate).

The contents of the autoclave were heated by means of electric windings, the temperature of the reaction being adjusted until the desired carbonylation rate was achieved. A liquid reaction composition stream was removed from the reactor under level control. The stream was cooled prior to reducing the pressure and separating the stream into a liquid phase and a gaseous phase which gaseous phase comprises unreacted carbon monoxide and gaseous by-products. The liquid phase was collected in a storage vessel and the gaseous phase was vented after on-line analysis by gas chromatography and cooling to remove condensibles. The liquid phase was periodically sampled on-line and was analysed off-line by gas chromatography.

To prevent build up of inert gases (from the feed and gaseous by-products) in the head space of the reactor, a high pressure bleed vent was provided. The gaseous stream removed via the high pressure bleed vent was cooled to remove condensibles and was vented after analysis by gas chromatography. Alternatively, this gaseous stream was combined with the gaseous phase derived from the liquid reaction composition stream for analysis.

The reaction was carried out at the desired temperature and pressure for a period of 6 to 7 hours.

EXPERIMENT N

The reaction was carried out at a constant total pressure of 27.6 barg (the partial pressures of carbon monoxide and hydrogen were calculated to be 12.5 and 0.17 bara respectively) and at a temperature of 194° C. The steady state reaction composition at a carbonylation rate of 8.3 mol/l/hr was as follows:

14% Methyl acetate
7% Water
2.6% Methyl Iodide
1000 ppm $IrCl_3.3H_2O$

This is not an example according to the present invention because no promoter was used.

EXAMPLE 18

The example demonstrates the promotional effect of introducing ruthenium promoter, 0.5 molar equivalents, to an iridium catalysed carbonylation reaction.

Experiment N was repeated except that ruthenium promoter ([Ru(CO)$_3$Cl$_2$]$_2$) was added to the liquid feed so as to achieve an iridium:ruthenium molar ratio in the reaction composition of 1:0.5. The temperature of the reaction was adjusted until the carbonylation rate was approximately the same as in Experiment N. The steady state reaction composition was as follows:

14.5% Methyl acetate
7.2% Water
2.2% Methyl iodide
1000 ppm iridium

It was found that at an iridium:ruthenium molar ratio of 1:0.5 a temperature of 191° C. was required to achieve a carbonylation rate of 8.0 mol/l/hr compared with a temperature of 194° C. to achieve a carbonylation rate of 8.3 mol/l/hr in the absence of ruthenium promoter (Experiment N).

The decrease in reaction temperature resulted in an increase in the calculated partial pressures of carbon monoxide and hydrogen in the reactor (13.4 and 0.19 bara respectively).

EXAMPLE 19

Example 18 was repeated except that the Ir:Ru molar ratio in the reaction composition was 1:1. The steady state reaction composition was as follows:

15.2% Methyl acetate
7.3% Water
2.1% Methyl Iodide
1000 ppm Iridium

It was found that at an iridium:ruthenium molar ratio of 1:1 a temperature of 188.5° C. was required to achieve a carbonylation rate of 8.1 mol/l/hr compared with a temperature of 191° C. to achieve a carbonylation rate of 8.0 mol/l/hr for Example 18 (iridium:ruthenium molar ratio of 1:0.5).

The further decrease in reaction temperature resulted in an increase in the calculated partial pressure of carbon monoxide and hydrogen in the reactor (13.9 and 0.22 bara respectively).

EXAMPLE 20

Experiment N was repeated except that ruthenium promoter was added to the liquid feed to achieve an iridium::ruthenium molar ratio of 1:1. The partial pressures of carbon monoxide and hydrogen in the reactor were calculated to be 12.6 and 0.2 bara respectively. A rate of 10.4 mol/l/hr was achieved at an steady state reaction composition of:

14.3% Methyl acetate
7.3% Water
2.1% Methyl iodide
1000 ppm Ir

This experiment shows that under these conditions, the presence of ruthenium promoter, at a molar ratio of iridium:ruthenium of 1:1 resulted in an increase in the carbonylation rate from 8.3 to 10.4 mol/l/hr (a 25% increase).

The methane make rate and water gas shift (WGS) reaction rate for Experiment N and Examples 18–20 are recorded in Table 6 together with the calculated concentration of propionic acid in the liquid phase of the liquid reaction composition (assuming all propionic acid precursors found in the product are converted to propionic acid).

TABLE 6

| | Gaseous and Propionic Acid By-Products | | | |
|---|---|---|---|---|
| Experiment | $CH_4$ make mol/l/hr | WGS mol/l/hr | WGS % of Rate | Propionic Acid ppm |
| N | 0.08 | 0.13 | 1.6 | 391 |
| 18 | 0.074 | 0.14 | 1.69 | 435 |
| 19 | 0.062 | 0.12 | 1.43 | 401 |
| 20 | 0.096 | 0.16 | 1.51 | 397 |

FURTHER EXPERIMENTS (CONTINUOUS OPERATION)

Methanol was continuously carbonylated in the presence of an iridium carbonylation catalyst, methyl iodide, optionally ruthenium carbonyl iodide reaction promoter, water and methyl acetate, in a 6 liter zirconium, stirred reactor with a working mass of 3.5 kg (measured at ambient temperature in a bubble free state) at a pressure between 25 and 30 barg (dependent on the required carbon monoxide partial pressure) and a temperature between 189° and 191° C. The temperature in the reactor was maintained by a hot oil jacket. Carbon monoxide was fed to the reactor on pressure demand via a sparge below the stirrer. Liquid reaction composition was continuously withdrawn from the reactor and passed to a flash tank operated at a pressure of 1.48 barg and a temperature of about 128° C. A vapour fraction comprising acetic acid product, propionic acid by-product, methyl iodide, methyl acetate and water passed overhead from the flash tank through an irrigated section and through a demister and was fed as a vapour into a distillation column. The liquid fraction from the flashtank comprising involatile catalyst, involatile promoter, acetic acid, water and the remainder of the methyl iodide and methyl acetate was recycled to the reactor. To maintain the required carbon monoxide partial pressure in the reactor a bleed of gas was optionally taken from the head space of the reactor.

The unit was operated with a corrosion metal removal system. A reactor product stream continuously was removed from the reactor upstream of the flashing valve. The stream was cooled to ambient temperature and depressurised across a control valve to 1.48 Barg. The stream was fed downflow to a corrosion metal removal bed at 400–500 ml/hr. The bed contained approximately 300 ml of a strong acid ion exchange resin (Amberlyst 15). The bed operated at 1.48 Barg and ambient temperature. The stream on exiting the bed was combined with the liquid fraction from the flashtank for return to the reactor. The bed was operated to maintain the level of corrosion metals in the reactor to <100 ppm total.

In the distillation column the acetic acid was removed from the base. The methyl iodide, methyl acetate and water, together with some of the acetic acid pass overhead and were condensed into two phases. The heavy, methyl iodide rich phase was recycled to the reactor. The lighter, aqueous phase was split: some used as reflux to the column, the remainder was recycled to the reactor. Methanol could be fed to the column to react with any hydrogen iodide present; the methyl iodide and water produced being removed overhead.

The non-condensables from the head of the column were first chilled to minimise the loss of volatiles from the process. The offgas steam was then passed to a scrubber where it was contacted countercurrently with chilled methanol. The methanol leaving the base of the scrubber was added to pure methanol and used as feed to the reactor.

The results (average compositions over at least 24 hours) from the experiments carried out on the above-described plant are given in table 7 below, which shows the benefits to reaction rate and reaction selectivity of using the reaction promoter ruthenium.

TABLE 7

| Exp. | [Ir] ppm | [Ru] ppm | Temp °C. | [MeI] wt % | [MeOAc] wt % | [$H_2O$] wt % | CO pp* bara | Carbn. Rate mol/l/hr | $CO_2$ Rate % of carbonylation | Propionic in acetic acid product ppm |
|---|---|---|---|---|---|---|---|---|---|---|
| P | 3240 | | 190.6 | 3.8 | 15.7 | 7.1 | 10.0 | 17.0 | 2.5 | 930 |
| Q | 1600 | | 190.0 | 5.3 | 15.8 | 7.0 | 8.1 | 11.0 | 1.5 | 530 |
| 21 | 1880 | 1130 | 190.0 | 4.8 | 15.0 | 6.8 | 8.0 | 12.8 | 1.7 | 690 |
| 22 | 2120 | 1790 | 189.5 | 4.8 | 15.1 | 7.0 | 8.1 | 17.4 | 1.7 | 640 |
| 23 | 1780 | 2320 | 190.0 | 5.1 | 15.1 | 7.2 | 8.3 | 17.1 | 1.6 | 600 |

*Based on analysis of combined low and high pressure off gas streams

We claim:

1. A process for the production of acetic acid by carbonylation of methanol or a reactive derivative thereof which process comprises contacting methanol or a reactive derivative thereof with carbon monoxide in a liquid reaction composition in a carbonylation reactor characterised in that the liquid reaction composition comprises:

(a) acetic acid, (b) an iridium catalyst, (c) methyl iodide,
   (d) at least a finite quantity of water, (e) methyl acetate
   and (f) as promoter, at least one of ruthenium and osmium.

2. A process as claimed in claim 1 in which the partial pressure of carbon monoxide in said reactor is less than 15 bar.

3. A process as claimed in claim 1 in which the molar ratio of promoter to iridium is in the range of 0.1:1 to 15:1.

4. A process as claimed in claim 3 in which the promoter is ruthenium.

5. A process as claimed in claim 1 in which the liquid reaction composition comprises 100 to 6000 ppm by weight iridium.

6. A process as claimed in claim 5 in which the molar ratio of promoter to iridium is in the range of 0.1:1 to 15:1.

7. A process as claimed in claim 6 in which the promoter is ruthenium.

8. A process as claimed in claim 1 in which the liquid reaction composition comprises from 0.1 to 15% by weight water.

9. A process as claimed in claim 1 in which the liquid reaction composition comprises from 1 to 20% by weight methyl iodide.

10. A process as claimed in claim 1 in which the liquid reaction composition comprises from 1 to 70% by weight methyl acetate.

11. A process as claimed in claim 1 in which the liquid reaction composition comprises 100 to 6000 ppm by weight iridium, 0.1 to 15% by weight water, 1 to 20% by weight methyl iodide and 1 to 70% by weight methyl acetate.

12. A process as claimed in claim 11 in which the molar ratio of promoter to iridium is in the range 0.1:1 to 15:1.

13. A process as claimed in claim 12 in which the promoter is ruthenium.

14. A process as claimed in claim 2 in which the molar ratio of promoter to iridium is in the range of 0.1:1 to 15:1.

15. A process as claimed in claim 2 in which the liquid reaction composition comprises 100 to 6000 ppm by weight iridium.

16. A process as claimed in claim 2 in which the liquid reaction composition comprises from 1 to 70% by weight methyl acetate.

17. A process as claimed in claim 2 in which the liquid reaction composition comprises from 1 to 20% by weight methyl iodide.

18. A process as claimed in claim 14 in which the promoter is ruthenium.

19. A process as claimed in claim 15 in which the molar ratio of promoter to iridium is in the range 0.1:1 to 15:1.

20. A process as claimed in claim 19 in which the promoter is ruthenium.

21. A process as claimed in claim 2 in which the liquid reaction composition comprises from 0.1 to 15% by weight water.

22. A process as claimed in claim 2 in which the liquid reaction composition comprises 100 to 6000 ppm by weight iridium, 0.1 to 15% by weight water, 1 to 20% by weight methyl iodide and 1 to 70% by weight methyl acetate.

23. A process as claimed in claim 22 in which the molar ratio of promoter to iridium is in the range 0.1:1 to 15:1.

24. A process as claimed in claim 23 in which the promoter is ruthenium.

25. A process as claimed in claim 1 in which the pressure of the carbonylation reaction is in the range 15 to 50 barg.

26. A process as claimed in claim 11 in which the pressure of the carbonylation reaction is in the range 15 to 50 barg.

27. A process as claimed in claim 13 in which the pressure of the carbonylation reaction is in the range 15 to 50 barg.

28. A process as claimed in claim 22 in which the pressure of the carbonylation reaction is in the range 15 to 50 barg.

29. A process as claimed in claim 24 in which the pressure of the carbonylation reaction is in the range 15 to 50 barg.

* * * * *

UNITED STATES PATENT AND TRADEMARK OFFICE
CERTIFICATE OF CORRECTION

PATENT NO. : 5,672,743
DATED : September 30, 1997
INVENTOR(S) : CARL S. GARLAND, MARTIN F. GILES and JOHN G. SUNLEY It is certified that error appears in the above-indentified patent and that said Letters Patent is hereby corrected as shown below:

Col. 2, l. 43, insert a comma (,) after "$IrI_3$" and before "$IrBr_3$"

Col. 5, l. 48, delete the number "15" after "of"

Signed and Sealed this

Thirteenth Day of January, 1998

Attest:

Attesting Officer

BRUCE LEHMAN

Commissioner of Patents and Trademarks